(12) United States Patent
Maka et al.

(10) Patent No.: US 12,115,237 B2
(45) Date of Patent: *Oct. 15, 2024

(54) SUBSTANTIALLY ANHYDROUS, CONCENTRATED SURFACTANT COMPOSITIONS

(71) Applicant: RITA CORPORATION, Crystal Lake, IL (US)

(72) Inventors: Katherine S. Maka, Inverness, IL (US); Ariella Tavor, Buffalo Grove, IL (US)

(73) Assignee: RITA CORPORATION, Crystal Lake, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/222,932

(22) Filed: Jul. 17, 2023

(65) Prior Publication Data

US 2023/0355486 A1 Nov. 9, 2023

Related U.S. Application Data

(63) Continuation of application No. 17/087,609, filed on Nov. 2, 2020, now Pat. No. 11,701,310.

(60) Provisional application No. 63/002,031, filed on Mar. 30, 2020, provisional application No. 62/929,738, filed on Nov. 1, 2019.

(51) Int. Cl.
| | | |
|---|---|---|
| *A61Q 19/10* | (2006.01) | |
| *A61K 8/04* | (2006.01) | |
| *A61K 8/34* | (2006.01) | |
| *A61K 8/37* | (2006.01) | |
| *A61K 8/44* | (2006.01) | |
| *A61K 8/60* | (2006.01) | |
| *A61Q 5/02* | (2006.01) | |

(52) U.S. Cl.
CPC .............. *A61K 8/046* (2013.01); *A61K 8/345* (2013.01); *A61K 8/375* (2013.01); *A61K 8/442* (2013.01); *A61K 8/602* (2013.01); *A61Q 5/02* (2013.01); *A61Q 19/10* (2013.01); *A61K 2800/596* (2013.01)

(58) Field of Classification Search
CPC ........ A61K 8/046; A61K 8/345; A61K 8/375; A61K 8/442; A61K 8/602; A61K 2800/596; A61K 8/33; A61K 8/44; A61K 8/39; A61K 8/604; A61K 2800/31; A61Q 5/02; A61Q 19/10; A61Q 5/12; A61Q 9/02; A61Q 11/00
USPC ....................................................... 510/126
See application file for complete search history.

(56) References Cited

U.S. PATENT DOCUMENTS

| | | |
|---|---|---|
| 4,469,627 A | 9/1984 | Trombone |
| 5,154,849 A | 10/1992 | Visscher et al. |
| 5,225,097 A | 7/1993 | Kacher et al. |
| 5,308,526 A | 5/1994 | Dias et al. |
| 5,312,559 A | 5/1994 | Kacher et al. |
| 5,358,667 A | 10/1994 | Bergmann |
| 5,518,647 A | 5/1996 | Zocchi |
| 5,911,981 A | 6/1999 | Dahms et al. |
| 6,132,746 A | 10/2000 | Hasenoehrl et al. |
| 6,362,145 B1 | 3/2002 | Littau et al. |
| 6,514,919 B2 | 2/2003 | Lambino et al. |
| 6,955,817 B2 | 10/2005 | McAtee et al. |
| 7,348,018 B2 | 3/2008 | McAtee et al. |
| 7,939,488 B2 | 5/2011 | Scheuing et al. |
| 8,084,409 B2 | 12/2011 | Lucka et al. |
| 8,673,117 B2 | 3/2014 | Rosencrance et al. |
| 8,877,184 B2 | 11/2014 | Potechin et al. |
| 9,409,853 B2 | 8/2016 | Schuch et al. |
| 9,480,629 B2 | 11/2016 | Kulkarni et al. |
| 9,758,746 B2 | 9/2017 | Meno |
| 9,861,571 B2 | 1/2018 | Bortolai et al. |
| 9,867,892 B2 | 1/2018 | Fischer |
| 9,993,408 B2 | 6/2018 | Fevola et al. |
| 10,610,477 B2 * | 4/2020 | Terrisse ................ A61K 8/345 |
| 2002/0006886 A1 | 1/2002 | Beerse et al. |
| 2008/0017339 A1 | 1/2008 | Zhang et al. |
| 2011/0171155 A1 | 7/2011 | Federle et al. |
| 2014/0031305 A1 * | 1/2014 | Terrisse ................ A61K 8/42 514/25 |
| 2016/0113849 A1 | 4/2016 | Grimadell et al. |
| 2016/0120803 A1 | 5/2016 | Mathur et al. |
| 2017/0209357 A1 | 7/2017 | Sirichandra |
| 2017/0239155 A1 | 8/2017 | Hartnett et al. |

(Continued)

FOREIGN PATENT DOCUMENTS

| | | | |
|---|---|---|---|
| CN | 104693031 A | 6/2015 | |
| EP | 2881381 A1 | 6/2015 | |
| FR | 2935608 A1 | 3/2010 | |
| KR | 102014935 B1 | 8/2019 | |
| KR | 20190108312 A | 9/2019 | |
| WO | WO 2012093102 A1 * | 7/2012 | ............. A61Q 1/14 |

OTHER PUBLICATIONS

Chinese Patent Application No. 202080077542.2, Office Action and Search Report, dated Jul. 12, 2023.

(Continued)

*Primary Examiner* — Eisa B Elhilo
(74) *Attorney, Agent, or Firm* — MARSHALL, GERSTEIN & BORUN LLP

(57) ABSTRACT

A substantially anhydrous, concentrated surfactant composition comprising a sugar-based surfactant; an amino acid based surfactant; a polyglycerol ester, a polyhydroxy ether, or a combination of a polyglycerol ester and a polyhydroxy ether; and, optionally, a glycol, wherein the substantially anhydrous surfactant composition contains less than about 12 weight percent of water.

35 Claims, No Drawings

(56) References Cited

U.S. PATENT DOCUMENTS

2017/0258701 A1 9/2017 Molenda et al.
2017/0360672 A1 12/2017 Maka et al.

OTHER PUBLICATIONS

Gentle Baby Cleansing Foam, TEN Gentle Baby Skincare, Mintel Product Sheet (Nov. 13, 2012).
International Application No. PCT/US2020/058611, International Search Report and Written Opinion, mailed Feb. 17, 2021.

* cited by examiner

SUBSTANTIALLY ANHYDROUS, CONCENTRATED SURFACTANT COMPOSITIONS

CROSS REFERENCE TO RELATED APPLICATION

This application is a continuation of U.S. patent application Ser. No. 17/087,609, filed Nov. 2, 2020, which claims the benefit under 35 U.S.C. § 119(e) of U.S. provisional patent application Ser. No. 62/929,738, filed Nov. 1, 2019, and U.S. provisional patent application Ser. No. 63/002,031, filed Mar. 30, 2020, the entire disclosures of which are hereby incorporated by reference in their entirety.

FIELD OF INVENTION

The present disclosure is directed to surfactant compositions, more particularly, to substantially anhydrous concentrated surfactant compositions which are capable of producing a stable foam. A method of generating a stable foam is also disclosed.

BACKGROUND OF INVENTION

Foam is an important property of cleaning compositions, especially for personal care compositions, such as hair shampoos, body gels, soaps, dentifrices, and shaving creams. Esthetically, foam is an important property because consumers equate a rich, long-lasting foam to a high quality product that works well. Functionally, foam is an important property because the foam first acts as a carrier to deliver cleaning surfactants to the skin or hair, then acts as a carrier to help remove emulsified soil and sebum from the cleaned skin or hair.

However, to achieve these esthetic and functional goals, the foam must be present in a wet, or spherical, form. If the generated foam is unstable, the foam changes from the wet form to the dry, or hexagonal, form relatively quickly, i.e., in less than about two minutes. Dry foam bubbles break quickly, and, therefore, for dermatogically preferred compositions do not provide the esthetic and functional foam properties typically required for consumer acceptance of the composition.

Foam is created by dispersing air or a gas in a surfactant-containing liquid. The mechanism of dispersing a gas in a surfactant-containing liquid is similar to the dispersion of two immiscible liquids during formation of an emulsion. Consequently, gas bubbles dispersed in a liquid are stabilized in the same manner as emulsions, i.e., by formation of surfactant layers at the gas-liquid interface. The surfactant layers keep the gas bubbles separated and prevent "coalescence," i.e., the merging of small gas bubbles to form larger gas bubbles. In general, more dense and more compact surfactant layers form smaller bubbles and retard the coalescence mechanism.

It is well known that because of the very large density difference between the dispersed gas and the liquid, the gas bubbles rise to the top of the liquid. The enriched concentration of gas bubbles at the top of the liquid appear as "foam." Initially, all of the gas bubbles in the foam are spherical, there is sufficient space between each individual spherical gas bubble for the presence of the surfactant-containing liquid, and the foam behaves like an emulsion. Such a foam is termed a "wet foam."

Over time, the liquid present in the interstices between the individual gas bubbles drains out due to gravity. Depending on the nature and chemical structure of the surfactant in the liquid, lamellar liquid crystalline layers form and arrange at the gas-liquid interface. If the lamellar layers have a low viscosity, the surfactant-containing liquid between individual gas bubbles can drain relatively easily, and the spherical form of the foam bubbles can change into a hexagonal form relatively quickly. Hexagonal bubbles quickly break. The transition of a foam from the spherical form to the hexagonal form due to foam aging can be observed visually. Foam in the hexagonal form is termed a "dry foam." Dry foams are unstable, which leads to a rapid reduction in foam volume due to rapidly breaking bubbles.

However, if the lamellar surfactant layers have a relatively higher viscosity, the transition from a spherical foam to the hexagonal form can be delayed. The speed of the transition of a foam from the spherical to hexagonal form determines how the foam is used in practical applications, and also determines how the foam is perceived esthetically. For example, for shampoos and shower gels, foams having a foam transition of about two minutes or less, i.e., a metastable foam structure, is desirable. Foam stability is controlled by many factors associated with the physiochemical properties of the surfactant solution such as surface tension, film surface tension (lamellar foams), surface viscosity and elasticity amongst others. A more stable foam could lead to insufficient wetting and distribution of the surfactant on the skin or hair, because during application of the shampoo or shower gel to the skin or hair, some parts of that foam undergo the transition to hexagonal state that allows the surfactant to drain from between the bubbles to contact and wet the hair or skin. Then, by continual rubbing of the shampoo or shower gel on the skin or hair, new foam bubbles are generated, which act as a carrier to lift and remove soil and sebum from the skin or hair and additional water rinses it off. Esthetically, spherical foam is desired. Functionally, the transition to the hexagonal form and regeneration of the spherical foam provides cleansing.

Other foam applications, e.g., shaving foams, require a foam having a much greater stability because the applied foam is not regenerated by continual rubbing techniques and because of the relatively long time required to complete the entire shaving operation. Furthermore, a controlled and sufficient wetting of the hair and skin is required for a smooth shaving operation. Sufficient wetting when a surfactant is foamed occurs only if the surfactant-containing liquid can drain from the foam lamellae to contact the skin, and drainage occurs more readily when the foam bubbles are in the spherical form.

The difference in structure between a wet, spherical foam and a dry, hexagonal foam is illustrated in FIGS. 3 and 4 of U.S. Pat. No. 5,911,811. FIG. 3 of U.S. Pat. No. 5,911,811 clearly shows both the lamellar liquid crystalline surfactant structure that stabilizes each bubble of a wet foam and the large amount of surfactant-containing liquid between individual bubbles. The relatively thick surfactant structure illustrated in FIG. 3 also retards the coalescence of neighboring bubbles into a single, larger bubble. In contrast, FIG. 4 of U.S. Pat. No. 5,911,811 shows a lack of a stabilizing surfactant structure around the hexagonal bubbles and the relative absence of surfactant-containing liquid between the bubbles.

The most commonly used sulfated anionic surfactants are well known for providing a high volume of a stable foam and having an excellent ability to emulsify soils and oils, i.e., to act as an efficient cleaner of skin and hair. Sulfated anionic surfactants include the anionic sulfates and the anionic sulfonates. As a result of these properties, sulfated anionic surfactants have been the primary surfactant used in shampoos and other skin and hair cleaning products. However, sulfated anionic surfactants have disadvantages. For example, the sulfated anionic surfactants strip the hair of natural oils that condition the hair and thereby can damage the hair and give freshly shampooed hair a dry feel. Sulfated anionic surfactants also are harsh to the skin and eyes, and thus sulfated anionic surfactants are generally unsuitable for use in baby shampoos and pet products.

Amphoteric and nonionic surfactants are relatively mild to the skin and eyes and do not strip the hair of natural oils. However, amphoteric and nonionic surfactants typically generate a poor foam in comparison to a sulfated anionic surfactant. Therefore, shampoos and similar cleaners based primarily on amphoteric and nonionic surfactants have not achieved good consumer acceptance. But, amphoteric and nonionic surfactants have been used in conjunction with sulfated anionic surfactants in attempts to provide a shampoo that takes advantage of the foaming properties of a sulfated anionic surfactant, while tempering the disadvantageous properties of the sulfated anionic surfactant with a nonionic or amphoteric surfactant. However, ethoxylated nonionic surfactants demonstrate poor biodegradability and, similar to sulfated anionic surfactants, are can also strip the hair of natural oils that condition the hair and thereby can damage the hair and give freshly shampooed hair a dry feel. Furthermore, dioxane is produced during their production and thus these surfactants are disfavored.

DETAILED DESCRIPTION

The disclosure provides substantially anhydrous concentrated surfactant compositions that are capable of producing a stable foam that remain in the wet, or spherical, form, preferably for at least as long as a comparable, conventional sulfated anionic surfactant-based product and/or a comparable, conventional ethoxylated surfactant-based product. Beneficially, the disclosed substantially anhydrous concentrated surfactant compositions are more environmentally friendly (particularly when compared with conventional sulfated- and/or ethoxylated-based surfactant compositions), all natural products that are not derived from petroleum products. For example, the disclosed substantially anhydrous concentrated surfactant compositions are preferably free of sulfated anionic surfactants (including but not limited to lauryl ether sulfates, lauryl sulfates, and sulfonates), free of phthalates, free of betaines, free of benzenes, free of silicones, free of preservatives (including but not limited to parabens (parahydroxybenzoates), phenoxyethanol, formaldehyde donors, Methylchloroisothiazolinone, Methylisothiazolinone, and urea), free of amines (including but not limited to nitrosamines, diethanolamines, monoethanol amines), free of formaldehyde, free of dioxanes (including but not limited to 1,4-dioxane), and/or free of ethylene oxide (e.g., the components are ethoxylate free and free of ethylene glycol). Further, the disclosed surfactant compositions advantageously do not typically cause adverse skin contact reactions and thus are suitable for a number of uses including but not limited to applications where a milder surfactant composition may be desired such as in baby shampoos and pet products.

Moreover, the disclosed substantially anhydrous concentrated surfactant compositions according to the disclosure can produce surprising amounts of foam in combination together, that is, the substantially anhydrous concentrated surfactant compositions according to the disclosure can advantageously demonstrate a synergistic foaming effect when compared with the individual constituent components thereof. Furthermore, in some aspects, the disclosed substantially anhydrous concentrated surfactant compositions according to the disclosure can demonstrate a shear-thickening effect that can advantageously stabilize a wet foam for a longer period of time, for example, when water is added to produce a foam, which can be particularly desirable for certain applications (e.g., when washing hair or applying a body wash). Such rheopectic fluids are a rare class of non-Newtonian fluids that exhibit a time-dependent increase in viscosity; they thicken or solidify when shaken or agitated. The longer a rheopectic fluid undergoes a shearing force, the higher its viscosity becomes, as the microstructure of a rheopectic fluid builds under continuous shearing (possibly due to shear-induced crystallization).

A significant advantage of the substantially anhydrous, concentrated surfactant compositions described herein is that they are compatible with environmentally friendly packaging including but not limited to packets or sachets comprising a bio-degradable material, for example, a bio-degradable water-soluble encapsulation film, a paper-based material, or a combination thereof. Suitable bio-degradable water-soluble encapsulation films may comprise polyvinyl alcohol (PVA), carboxymethylcellulose (CMC), alginate, chitosan, starch, polylactic acid (PLA), and poly(lactic-co-glycolic acid) (PGLA), or other materials that dissolve rapidly in water for facilitating single use applications. Waxed paper packets that can be composted are also suitable for single use applications. Thus, the substantially anhydrous concentrated surfactant compositions disclosed herein can reduce the utilization of costly packaging that can also be harmful to the environment. Typically, 1 gram to 5 grams of a substantially anhydrous, concentrated surfactant composition can be encapsulated into a water soluble film or a waxed paper packet for single use applications. Of course, the substantially anhydrous, concentrated surfactant compositions can also be used in multi-use dispensers including those often found in bathrooms, showers, and the like, while reducing the amount of packaging needed for the same number of uses relative to conventional, less concentrated compositions.

As used herein, the term "free of" means that a component is not intentionally added to a substantially anhydrous surfactant composition according to the disclosure, but may be present as a by-product or contaminant such that a surfactant composition according to the disclosure may contain up to about 0.1% by weight of the specific component based on the weight of the substantially anhydrous surfactant composition.

As used herein, the terms "substantially anhydrous" and "substantially free of water" mean that the substantially anhydrous surfactant compositions according to the disclosure contain relatively insignificant amounts of water (at least when compared to conventional surfactant compositions). For example, the substantially anhydrous surfactant compositions according to the disclosure may contain less than about 12 weight percent ("wt. %"), less than about 10 wt. %, less than about 7.5 wt. %, and/or less than about 5 wt. % of water, based on the entire weight of the composition.

As used herein, the term "about" means+/−10% of any recited value, or in an alternative embodiment, +/−5% of any recited value. As used herein, this term modifies any recited value, range of values, or endpoints of one or more ranges.

In one embodiment, the disclosure provides a substantially anhydrous surfactant composition comprising a sugar-based surfactant, and an amino acid based surfactant, and optionally, a glycol, wherein the substantially anhydrous surfactant composition contains less than about 12 weight percent of water. In one refinement, the substantially anhydrous surfactant composition may further comprise a polyglycerol ester (also referred to as "polyglyceryl esters" according to INCI nomenclature). In an additional refinement, the substantially anhydrous surfactant composition may further comprise a polyhydroxy ether. In yet another refinement, the substantially anhydrous surfactant composition may further comprise a polyglycerol ester and a polyhydroxy ether.

In another embodiment, the disclosure provides a method of generating a stable, wet foam comprising adding a surfactant blend according to the disclosure to an aqueous composition to provide an aqueous mixture, and forming bubbles from the aqueous mixture of step to generate the stable, wet foam.

When a weight percent is described herein, it is described with respect to 100% active components. As a result, the weight percents described herein may also be described as the "percent actives" of a given component based on the entire weight of the composition.

The sugar-based surfactant may be selected from a C8-C16 alkyl glucoside, a C8-C16 alkyl polyglucoside, or a combination of a C8-C16 alkyl glucoside and a C8-C16 alkyl polyglucoside. The sugar-based surfactant comprising at least one of a C8-C16 alkyl glucoside and/or a C8-C16 alkyl polyglucoside may be a non-ionic sugar-based (i.e., glucose-based) surfactant but may also be a salt of a sugar-based surfactant. Combinations of non-ionic sugar-based surfactants and salts of sugar-based surfactants may also be used as the sugar-based surfactant. The sugar-based surfactant may be present in the substantially anhydrous surfactant compositions according to the disclosure in an amount between about 5 weight percent (wt. %) and about 50 wt. %, between about 7.5 weight percent (wt. %) and about 50 wt. %, between about 10 weight percent (wt. %) and about 50 wt. %, between about 10 weight percent (wt. %) and about 40 wt. %, between about 15 wt. % and about 30 wt. %, and/or between 17.5 wt. % and about 25 wt. %, for example, about 20 wt. %, based on the total weight of the composition.

The sugar-based surfactant can be prepared/derived from the 6-carbon monosaccharide glucose and C8-C16 alcohols. Suitable C8-C16 alkyl glucosides include but are not limited to: decyl glucoside, heptyl glucoside, octyl glucoside, lauryl glucoside (or dodecyl glucoside), coco-glucosides (which is a mixture of C8-C16 alkyl glucosides), and combinations thereof. Suitable C8-C16 alkyl polyglucosides include but are not limited to: disodium coco-glucoside citrate, sodium coco-glucoside tartrate, sodium coco-glucoside succinate, and combinations thereof. Combinations of one or more C8-C16 alkyl glucosides and one or more C8-C16 alkyl polyglucosides may also be used. C8-C16 alkyl polyglucosides, particularly disodium coco-glucoside citrate, are preferred sugar-based surfactants for use in the substantially anhydrous concentrate surfactant compositions according to the disclosure.

The amino acid based surfactant is an anionic surfactant derived from an amino acid and a C8-C16 fatty acid. Typically, the amino acid based surfactant is derived from an amino acid such as sarcosine, glutamine, glycine, alanine, or glycine. C8-C16 acyl sarcosinates, C8-C16 acyl glutamates, C8-C16 acyl alaninates, and/or C8-C16 acyl glycinates are suitable amino acid surfactants. The amino acid based surfactant may be present in the substantially anhydrous surfactant compositions disclosed herein in an amount between about 10 weight percent (wt. %) and about 40 wt. %, between about 10 wt. % and about 30 wt. %, between about 15 wt. % and about 30 wt. %, and/or between 17.5 wt. % and about 25 wt. %, for example, about 20 wt. %, based on the entire weight of the composition.

Suitable C8-C16 acyl sarcosinates include but are not limited to: sodium lauroyl sarcosinate, sodium cocoyl sarcosinate (which is a mixture of sodium C8-C16 acyl sarcosinates), sodium myristoyl sarcosinate, ammonium lauroyl sarcosinate, ammonium cocoyl sarcosinate, isopropyl lauroyl sarcosinate, potassium cocoyl sarcosinate, potassium lauroyl sarcosinate, and combinations thereof; suitable C8-C16 acyl glutamates include but are not limited to: sodium lauroyl glutamate, sodium cocoyl glutamate (which is a mixture of sodium C8-C16 acyl glutamates), sodium myristoyl glutamate, ammonium lauroyl glutamate, ammonium cocoyl glutamate, isopropyl lauroyl glutamate, potassium cocoyl glutamate, potassium lauroyl glutamate, and combinations thereof; suitable C8-C16 acyl alaninates include but are not limited to: sodium lauroyl alaninate, sodium cocoyl alaninate (which is a mixture of sodium C8-C16 acyl alaninate), sodium myristoyl alaninate, ammonium lauroyl alaninate, ammonium cocoyl alaninate, isopropyl lauroyl alaninate, potassium cocoyl alaninate, potassium lauroyl alaninate, and combinations thereof; suitable C8-C16 acyl glycinates include but are not limited to: sodium lauroyl glycinate, sodium cocoyl glycinate (which is a mixture of sodium C8-C16 acyl glycinates), sodium myristoyl glycinate, ammonium lauroyl glycinate, ammonium cocoyl glycinate, isopropyl lauroyl glycinate, potassium cocoyl glycinate, potassium lauroyl glycinate, and combinations thereof. For example, a combination of one or more C8-C16 acyl sarcosinates and one or more C8-C16 acyl glycinates may be used. Similarly, for example, a combination of one or more C8-C16 acyl sarcosinates and one or more C8-C16 acyl alaninates may be used. Combinations of one or more C8-C16 acyl sarcosinates, one or more C8-C16 acyl glutamates, one or more C8-C16 acyl alaninates, and one or more C8-C16 acyl glycinates also may be used. C8-C16 acyl sarcosinates, particularly sodium lauroyl sarcosinate, are preferred amino acid based surfactants for use in the substantially anhydrous concentrate surfactant compositions according to the disclosure.

In one preferred embodiment, a C8-C16 acyl sarcosinate is preferred because its solubility in glycols and/or polyhydroxyethers allows the amount of water to be minimized. In a further preferred embodiment, the disclosed substantially anhydrous surfactant compositions are free of sodium cocoyl isethionate, sodium lauroyl glutamate, sodium cocoyl glycinate, and/or potassium cocoyl glycinate.

When included, the polyglycerol ester is a significant component in that it can provide foam boosting synergy as well as shear-thickening properties to the substantially anhydrous surfactant compositions disclosed herein, specifically relative to a combination of the other components of the composition. Incorporation of the polyglycerol ester component into the substantially anhydrous surfactant compositions disclosed herein also advantageously solubilizes the various other components, thereby minimizing the amount of water and/or glycol carrier solvent in the compositions. The polyglycerol ester may be present in the substantially anhydrous surfactant compositions according to the disclosure in an amount between about 15 weight percent (wt. %) and about 45 wt. %, between about 20 wt. % and about 40 wt. %, and/or between 25 wt. % and about 35 wt. %, for example about 30 wt. %. Suitable polyglycerol esters include but are not limited to polyglycerol-2-caprate, polyglycerol-2 caprylate, polyglycerol-3-caprate, polyglycerol-3 caprylate, polyglycerol-2-laurate, polyglycerol-3-laurate, polyglycerol-3 cocoate, polyglycerol-4 caprate, polyglycerol-4 caprylate, polyglycerol-4 laurate, polyglycerol-4 cocoate, and combinations of the foregoing. In one aspect, the polyglycerol ester is the primary surfactant in the composition, i.e., the polyglycerol ester is present in an amount greater than any other surfactant in the composition (based on the amount of actives present in the composition). Polyglycerol-2-caprate is a preferred polyglycerol ester for use in the substantially anhydrous concentrate surfactant compositions according to the disclosure.

When included, the polyhydroxy ether is also a significant component in that it can provide foam boosting synergy to the substantially anhydrous surfactant compositions disclosed herein, specifically relative to a combination of the other components of the composition. Incorporation of the polyhydroxy ether component into the substantially anhydrous surfactant compositions disclosed herein also advantageously solubilizes the various other components, thereby minimizing the amount of water and/or glycol carrier solvent in the compositions. The polyhydroxy ether may be present in the substantially anhydrous surfactant compositions according to the disclosure in an amount between about 10 weight percent (wt. %) and about 45 wt. %, between about 15 wt. % and about 40 wt. %, and/or between 20 wt. % and about 35 wt. %, for example about 25 wt. %. Suitable polyhydroxy ethers include but are not limited to glycerol ethers, alkyl glycerols, and combinations of the foregoing. Generally, the alkyl groups of the glycerol ethers and alkyl glycerols include five carbon atoms or less. In one aspect, the polyhydroxy ether is the primary surfactant in the composition, i.e., the polyhydroxy ether is present in an amount greater than any other surfactant in the composition (based on the amount of actives present in the composition). Diglycerine, also known as diglycerol, more formally known as (3-(2,3-dihydroxypropoxy)propane-1,2-diol), is a preferred polyhydroxy ether for use in the substantially anhydrous concentrate surfactant compositions according to the disclosure.

Because the amino acid based surfactant of the substantially anhydrous, concentrated surfactant compositions according to the disclosure is generally a powder, a carrier is typically needed to help solubilize the composition. A glycol is therefore typically included in the substantially anhydrous surfactant compositions according to the disclosure in an amount between about 10 weight percent (wt. %) and less than 40 wt. %, between about 15 wt. % and about 35 wt. %, between 20 wt. % and about 35 wt. %, and/or between 20 wt. % and about 30 wt. %, for example about 25 wt. % or about 30 wt. %. Suitable glycols include but are not limited to propylene glycol, dipropylene glycol, propanediol, and combinations thereof. Amounts of glycol greater than 40 wt. % should be avoided. In addition, the substantially anhydrous, concentrated surfactant compositions according to the disclosure may contain less than 5 wt. % or more preferably may be free of other glycols such as butylene glycol, pentylene glycol, hexylene glycol, and glycerin.

Preservatives and/or biocides need not be included in the substantially anhydrous concentrated surfactant compositions. Thus, the substantially anhydrous concentrated surfactant compositions can be free of preservatives and biocides.

Optionally, a C8-C14 acyl lactylate may be included in the substantially anhydrous concentrated surfactant compositions according to the disclosure. The C8-C14 acyl lactylate is an anionic surfactant that typically serves as a foam booster and viscosity enhancer in the surfactant compositions according to the disclosure. The C8-C14 acyl lactylate may be present in the surfactant compositions according to the disclosure in an amount between about 0 weight percent (wt. %) and about 10 wt. %, between about 0 wt. % and about 7.5 wt. %, and/or between 1 wt. % and about 4 wt. %. The C8-C14 acyl lactylate can be prepared by reacting a C8-C14 fatty acid with lactic acid. Suitable C8-C14 acyl lactylates include but are not limited to: sodium caproyl lactylate, sodium lauroyl lactylate, sodium myristoyl lactylate, and combinations thereof. Of course, other salts including but not limited to ammonium and potassium salts may also be used.

The surfactant compositions according to the disclosure may be used in a number of different personal care compositions. In particular, the surfactant compositions according to the disclosure can be incorporated into shaving foams, dentrifices, shampoos, shower gels, soaps (both liquid and bars; facial cleaners; hand washes; body washes), and hair care foams such as mousses and dyes.

In embodiments, the disclosed substantially anhydrous surfactant compositions are free of betaines and/or sulfonated surfactants. For example, the disclosed substantially anhydrous surfactant compositions can be free of disodium lauryl sulfosuccinate, sodium C14-16 olefin sulfonate, and/or lauramidopropyl betaine.

In embodiments, the disclosed substantially anhydrous surfactant compositions are free of preservatives such as methylchloroisothiazolinone, methylisothiazolinone, sodium dehydroacetate, and/or dehydroacetic acid.

In embodiments, the disclosed substantially anhydrous surfactant compositions are free of colorants such as red #40, blue #1, and even natural colorants such as beetroot, beta carotene, purple potato, and/or black carrot.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

In addition, uses of "a" or "an" are employed to describe elements and components of the embodiments described herein. This is done merely for convenience and to give a general sense of the description. This description, and the claims that follow, should be read to include one or at least one, and the singular also includes the plural unless it is clear that it is meant otherwise.

Although the foregoing text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Example 1

A surfactant composition according to the disclosure was prepared by combining the following components in the amounts shown in Table 1.

TABLE 1

| Raw Material | amount (wt. %) |
| --- | --- |
| Disodium Coco-Glucoside Citrate | 20.10 |
| Sodium Lauroyl Sarcosinate | 19.80 |
| Polyglycerol-2-Caprate | 30.00 |
| Propylene Glycol | 25.10 |
| Water | 5.00 |

The substantially anhydrous, concentrated surfactant composition was found to have excellent foaming properties and to cause no skin irritation upon application.

The viscosities of 5 batches of the foregoing surfactant composition were measured, demonstrating the shear-thickening behavior of the surfactant compositions as the viscosities increased over time. The data below shows the difference between viscosity measurements at 3 minutes and at 1 minute at different spindle speeds (using Spindle #3), thereby confirming this advantageous feature of the surfactant compositions according to the disclosure. Thus, this surfactant composition exhibits rheopectic behavior where the viscosity increases with time at the same shear rate. This effect is perceivable during use of the surfactant composition once water is added, whether to a shampoo, hand soap, or body wash comprising the surfactant composition according to this example.

$\Delta v = v_3 \text{ minutes} - v_1 \text{ minute}$

Spindle #3

| RPM | Average $\Delta v$ cps (22C) | Standard deviation cps | Relative standard deviation (RSD) |
| --- | --- | --- | --- |
| 1 | 110 | 22 | 20% |
| 2 | 118 | 33 | 28% |
| 5 | 172 | 39 | 23% |
| 10 | 52 | 16 | 32% |
| 20 | 29 | 7 | 26% |

The temperature of a mixture containing the surfactant composition according to Example 1 and added water was monitored. In the following experiments, as the surfactant composition is added to water, the temperature increases by 4° C.

100 g of water at 25° C.+30-50 g of the surfactant composition of Example 1 at 25° C.; the resulting temperature after mixing for 1 minutes is 29° C.

100 g of water at 20° C.+30-50 g of the surfactant composition of Example 1 at 20° C.; the resulting temperature after mixing for 1 minutes is 24° C.

The demonstrated increase in temperature is easily perceptible to the consumer such that they can actually feel this change when the composition is applied, creating an experience in which the consumer can perceive the product is performing its intended cleaning purpose.

Example 2

An additional surfactant composition according to the disclosure was prepared by combining the following components in the amounts shown in Table 2.

TABLE 2

| Raw Material | amount (wt. %) |
| --- | --- |
| Disodium Coco-Glucoside Citrate | 20.10 |
| Sodium Lauroyl Sarcosinate | 19.80 |
| Diglycerine | 25.00 |
| Propylene Glycol | 30.10 |
| Water | 5.00 |

The substantially anhydrous, concentrated surfactant composition was found to have excellent foaming properties and to cause no skin irritation upon application.

The viscosities of 5 batches of the foregoing surfactant composition were measured, demonstrating the shear-thickening behavior of the surfactant compositions as the viscosities increased over time. The data below shows the difference between viscosity measurements at 3 minutes and at 1 minute at different spindle speeds (using Spindle #5), thereby confirming this advantageous feature of the surfactant compositions according to the disclosure. Thus, this surfactant composition exhibits rheopectic behavior where the viscosity increases with time at the same shear rate. This effect is perceivable during use of the surfactant composition once water is added, whether to a shampoo, hand soap, or body wash comprising the surfactant composition according to this example.

$\Delta v = v_3 \text{ minutes} - v_1 \text{ minute}$

Spindle #5

| RPM | Average $\Delta v$ cps (22C) | Standard deviation cps | Relative standard deviation |
| --- | --- | --- | --- |
| 20 | 146 | 9 | 6% |
| 50 | 156 | 11 | 7% |
| 100 | 940 | 114 | 12% |

The temperature of a mixture containing the surfactant composition according to Example 1 and added water was monitored. In the following experiments, as the surfactant composition is added to water, the temperature increases by 4° C.

100 g of water at 25° C.+30-50 g of the surfactant composition of Example 2 at 25° C.; the resulting temperature after mixing for 1 minutes is 29° C.

100 g of water at 20° C.+30-50 g of the surfactant composition of Example 2 at 20° C.; the resulting temperature after mixing for 1 minutes is 24° C.

The demonstrated increase in temperature is easily perceptible to the consumer such that they can actually feel this change when the composition is applied, creating an experience in which the consumer can perceive the product is performing its intended cleaning purpose.

What is claimed:

1. A substantially anhydrous, concentrated surfactant composition comprising:
   a sugar-based surfactant;
   an amino acid based surfactant;
   at least one polyglycerol ester or at least one polyhydroxy ether; and,
   a glycol,
   wherein the substantially anhydrous surfactant composition is a rheopectic fluid containing less than about 12 weight percent of water, and the amino acid based surfactant is derived from an amino acid chosen from one or more in the group of sarcosine, glutamine, glycine, alanine, and glycine.

2. A substantially anhydrous, concentrated surfactant composition comprising:
a sugar-based surfactant;
an amino acid based surfactant;
a polyglycerol ester; and,
a glycol,
wherein the substantially anhydrous surfactant composition is a rheopectic fluid containing less than about 12 weight percent of water, and the sugar-based surfactant comprises a C8-C16 alkyl glucoside, a C8-C16 alkyl polyglucoside, or a combination of a C8-C16 alkyl glucoside and a C8-C16 alkyl polyglucoside.

3. The substantially anhydrous, concentrated surfactant composition according to claim 2, wherein the sugar-based surfactant comprises decyl glucoside, heptyl glucoside, octyl glucoside, lauryl glucoside, coco-glucosides, disodium coco-glucoside citrate, sodium coco-glucoside tartrate, sodium coco-glucoside succinate, or any combination thereof.

4. The substantially anhydrous, concentrated surfactant composition according to claim 2, wherein the sugar-based surfactant is present in an amount between about 5 weight percent (wt. %) and about 50 wt. %, based on the entire weight of the composition.

5. The substantially anhydrous, concentrated surfactant composition according to claim 2, wherein the amino acid based surfactant is derived from an amino acid chosen from one or more in the group of sarcosine, glutamine, glycine, alanine, and glycine.

6. The substantially anhydrous, concentrated surfactant composition according to claim 2, wherein the amino acid based surfactant comprises a C8-C16 acyl sarcosinate, a C8-C16 acyl glutamate, a C8-C16 acyl alaninate, a C8-C16 acyl glycinate, or any combination thereof.

7. The substantially anhydrous, concentrated surfactant composition according to claim 2, wherein the amino acid based surfactant comprises one or more amino acid based surfactants chosen from the group of sodium lauroyl sarcosinate, sodium cocoyl sarcosinate, sodium myristoyl sarcosinate, ammonium lauroyl sarcosinate, ammonium cocoyl sarcosinate, isopropyl lauroyl sarcosinate, potassium cocoyl sarcosinate, potassium lauroyl sarcosinate, sodium lauroyl glutamate, sodium cocoyl glutamate, sodium myristoyl glutamate, ammonium lauroyl glutamate, ammonium cocoyl glutamate, isopropyl lauroyl glutamate, potassium cocoyl glutamate, potassium lauroyl glutamate, sodium lauroyl alaninate, sodium cocoyl alaninate, sodium myristoyl alaninate, ammonium lauroyl alaninate, ammonium cocoyl alaninate, isopropyl lauroyl alaninate, potassium cocoyl alaninate, potassium lauroyl alaninate, sodium lauroyl glycinate, sodium cocoyl glycinate, sodium myristoyl glycinate, ammonium lauroyl glycinate, ammonium cocoyl glycinate, isopropyl lauroyl glycinate, potassium cocoyl glycinate, and potassium lauroyl glycinate.

8. The substantially anhydrous, concentrated surfactant composition according to claim 2, wherein the amino acid based surfactant is present in an amount between about 10 weight percent (wt. %) and about 40 wt. %, based on the entire weight of the composition.

9. The substantially anhydrous, concentrated surfactant composition according to claim 2, wherein the polyglycerol ester comprises polyglycerol-2-caprate, polyglycerol-2 caprylate, polyglycerol-3-caprate, polyglycerol-3 caprylate, polyglycerol-2-laurate, polyglycerol-3-laurate, polyglycerol-3 cocoate, polyglycerol-4 caprate, polyglycerol-4 caprylate, polyglycerol-4 laurate, polyglycerol-4 cocoate, or any combination thereof.

10. The substantially anhydrous, concentrated surfactant composition according to claim 2, wherein the polyglycerol ester is the primary surfactant in the composition.

11. The substantially anhydrous, concentrated surfactant composition according to claim 2, wherein the polyglycerol ester is present in an amount between about 10 weight percent (wt. %) and about 45 wt. %, based on the entire weight of the composition.

12. The substantially anhydrous, concentrated surfactant composition according to claim 2, wherein the glycol comprises one or more glycols chosen from the group of propylene glycol, dipropylene glycol, and propanediol.

13. The substantially anhydrous, concentrated surfactant composition according to claim 2, wherein the glycol is present in an amount between about 10 weight percent (wt. %) and about 40 wt. %, based on the entire weight of the composition.

14. The substantially anhydrous, concentrated surfactant composition according to claim 2, wherein the substantially anhydrous, concentrated surfactant composition contains less than 5 wt. % of glycols other than propylene glycol, dipropylene glycol, propanediol, or any combination thereof, based on the entire weight of the composition.

15. The substantially anhydrous, concentrated surfactant composition according to claim 2, wherein the substantially anhydrous, concentrated surfactant composition contains less than about 10 wt. % water, based on the entire weight of the composition.

16. A personal care composition comprising the substantially anhydrous, concentrated surfactant composition according to claim 2.

17. The personal care composition according to claim 16, wherein the personal care composition is selected from the group consisting of shaving foams, dentifrices, shampoos, shower gels, soaps, and hair care foams.

18. A substantially anhydrous, concentrated surfactant composition comprising:
a sugar-based surfactant;
an amino acid based surfactant;
a polyglycerol ester; and,
a polyhydroxy ether,
wherein the substantially anhydrous surfactant composition is a rheopectic fluid containing less than about 12 weight percent of water, and the sugar-based surfactant comprises a C8-C16 alkyl glucoside, a C8-C16 alkyl polyglucoside, or a combination of a C8-C16 alkyl glucoside and a C8-C16 alkyl polyglucoside.

19. The substantially anhydrous, concentrated surfactant composition according to claim 18, wherein the sugar-based surfactant comprises decyl glucoside, heptyl glucoside, octyl glucoside, lauryl glucoside, coco-glucosides, disodium coco-glucoside citrate, sodium coco-glucoside tartrate, sodium coco-glucoside succinate, or any combination thereof.

20. The substantially anhydrous, concentrated surfactant composition according to claim 18, wherein the sugar-based surfactant is present in an amount between about 5 weight percent (wt. %) and about 50 wt. %, based on the entire weight of the composition.

21. The substantially anhydrous, concentrated surfactant composition according to claim 18, wherein the amino acid based surfactant is derived from an amino acid chosen from one or more in the group of sarcosine, glutamine, glycine, alanine, and glycine.

22. The substantially anhydrous, concentrated surfactant composition according to claim 18, wherein the amino acid based surfactant comprises a C8-C16 acyl sarcosinate, a C8-C16 acyl glutamate, a C8-C16 acyl alaninate, a C8-C16 acyl glycinate, or any combination thereof.

23. The substantially anhydrous, concentrated surfactant composition according to claim 18, wherein the amino acid based surfactant comprises one or more amino acid based surfactants chosen from the group of sodium lauroyl sarcosinate, sodium cocoyl sarcosinate, sodium myristoyl sarcosinate, ammonium lauroyl sarcosinate, ammonium cocoyl sarcosinate, isopropyl lauroyl sarcosinate, potassium cocoyl sarcosinate, potassium lauroyl sarcosinate, sodium lauroyl glutamate, sodium cocoyl glutamate, sodium myristoyl glutamate, ammonium lauroyl glutamate, ammonium cocoyl glutamate, isopropyl lauroyl glutamate, potassium cocoyl glutamate, potassium lauroyl glutamate, sodium lauroyl alaninate, sodium cocoyl alaninate, sodium myristoyl alaninate, ammonium lauroyl alaninate, ammonium cocoyl alaninate, isopropyl lauroyl alaninate, potassium cocoyl alaninate, potassium lauroyl alaninate, sodium lauroyl glycinate, sodium cocoyl glycinate, sodium myristoyl glycinate, ammonium lauroyl glycinate, ammonium cocoyl glycinate, isopropyl lauroyl glycinate, potassium cocoyl glycinate, and potassium lauroyl glycinate.

24. The substantially anhydrous, concentrated surfactant composition according to claim 18, wherein the amino acid based surfactant is present in an amount between about 10 weight percent (wt. %) and about 40 wt. %, based on the entire weight of the composition.

25. The substantially anhydrous, concentrated surfactant composition according to claim 18, wherein the polyglycerol ester comprises polyglycerol-2-caprate, polyglycerol-2 caprylate, polyglycerol-3-caprate, polyglycerol-3 caprylate, polyglycerol-2-laurate, polyglycerol-3-laurate, polyglycerol-3 cocoate, polyglycerol-4 caprate, polyglycerol-4 caprylate, polyglycerol-4 laurate, polyglycerol-4 cocoate, or any combination thereof.

26. The substantially anhydrous, concentrated surfactant composition according to claim 18, wherein the substantially anhydrous, concentrated surfactant composition contains less than about 10 wt. % water, based on the entire weight of the composition.

27. A personal care composition comprising the substantially anhydrous, concentrated surfactant composition according to claim 18.

28. The personal care composition according to claim 27 wherein the personal care composition is selected from the group consisting of shaving foams, dentifrices, shampoos, shower gels, soaps, and hair care foams.

29. A substantially anhydrous, concentrated surfactant composition comprising:
a sugar-based surfactant;
an amino acid based surfactant; and,
a polyglycerol ester, a polyhydroxy ether, or a combination of a polyglycerol ester and a polyhydroxy ether,
wherein the substantially anhydrous surfactant composition is a rheopectic fluid containing less than about 12 weight percent of water, wherein the substantially anhydrous, concentrated surfactant composition is free of propylene glycol, dipropylene glycol, propanediol, or any combination thereof.

30. The substantially anhydrous, concentrated surfactant composition according to claim 29, wherein the substantially anhydrous, concentrated surfactant composition is free of glycol.

31. The substantially anhydrous, concentrated surfactant composition according to claim 29, comprising a combination of the polyglycerol ester and the polyhydroxy ether.

32. The substantially anhydrous, concentrated surfactant composition according to claim 29, wherein the polyglycerol ester is present and comprises polyglycerol-2-caprate.

33. The substantially anhydrous, concentrated surfactant composition according to claim 29, wherein the polyhydroxy ether is present and comprises diglycerine.

34. The substantially anhydrous, concentrated surfactant composition according to claim 29, wherein the amino acid based surfactant comprises sodium lauroyl sarcosinate.

35. The substantially anhydrous, concentrated surfactant composition according to claim 29, wherein the sugar-based surfactant comprises decyl glucoside, heptyl glucoside, octyl glucoside, lauryl glucoside, coco-glucosides, disodium coco-glucoside citrate, sodium coco-glucoside tartrate, sodium coco-glucoside succinate, or any combination thereof.

* * * * *